United States Patent [19]

Baile et al.

[11] Patent Number: 4,689,420

[45] Date of Patent: Aug. 25, 1987

[54] PROCESS FOR PREPARATION OF CYCLOPOLYDIORGANOSILOXANES

[75] Inventors: Gnaneshwar R. Baile; Jane A. Crompton; Daniel F. McMahon, all of Midland, Mich.

[73] Assignee: Dow Corning Corporation, Midland, Mich.

[21] Appl. No.: 799,704

[22] Filed: Nov. 19, 1985

[51] Int. Cl.$^4$ ............................................. C07F 7/08
[52] U.S. Cl. .................................... 556/460; 556/461
[58] Field of Search ................................. 556/460, 461

[56] References Cited

U.S. PATENT DOCUMENTS

| | | | |
|---|---|---|---|
| 2,934,550 | 4/1960 | Jack | 556/460 |
| 3,347,895 | 10/1967 | Omietanski et al. | 556/461 |
| 3,358,009 | 12/1967 | Omietanski et al. | 556/461 |
| 4,197,251 | 4/1980 | Hirakawa et al. | 556/460 |
| 4,539,418 | 9/1985 | Takago et al. | 556/460 X |

Primary Examiner—Paul F. Shaver

[57] ABSTRACT

What is disclosed is a process for converting polydiorganosiloxanes to cyclopolydiorganosiloxanes with reduced cleavage of organic groups from silicon atoms. The process comprises (A) feeding a mixture of the polydiorganosiloxanes, a catalyst, and an organic solvent to a device in which water is formed as the polydiorganosiloxanes react in the presence of the catalyst and the organic solvent, the water formed being driven out of said device as a two-phase organic solvent/water azeotrope; (B) reacting the polydiorganosiloxane/catalyst/organic solvent mixture from (A), essentially free of water, to convert the polydiorganosiloxanes to the desired product cyclopolydiorganosiloxanes; and (C) recovery of the desired product cyclopolydiorganosiloxanes.

24 Claims, 1 Drawing Figure

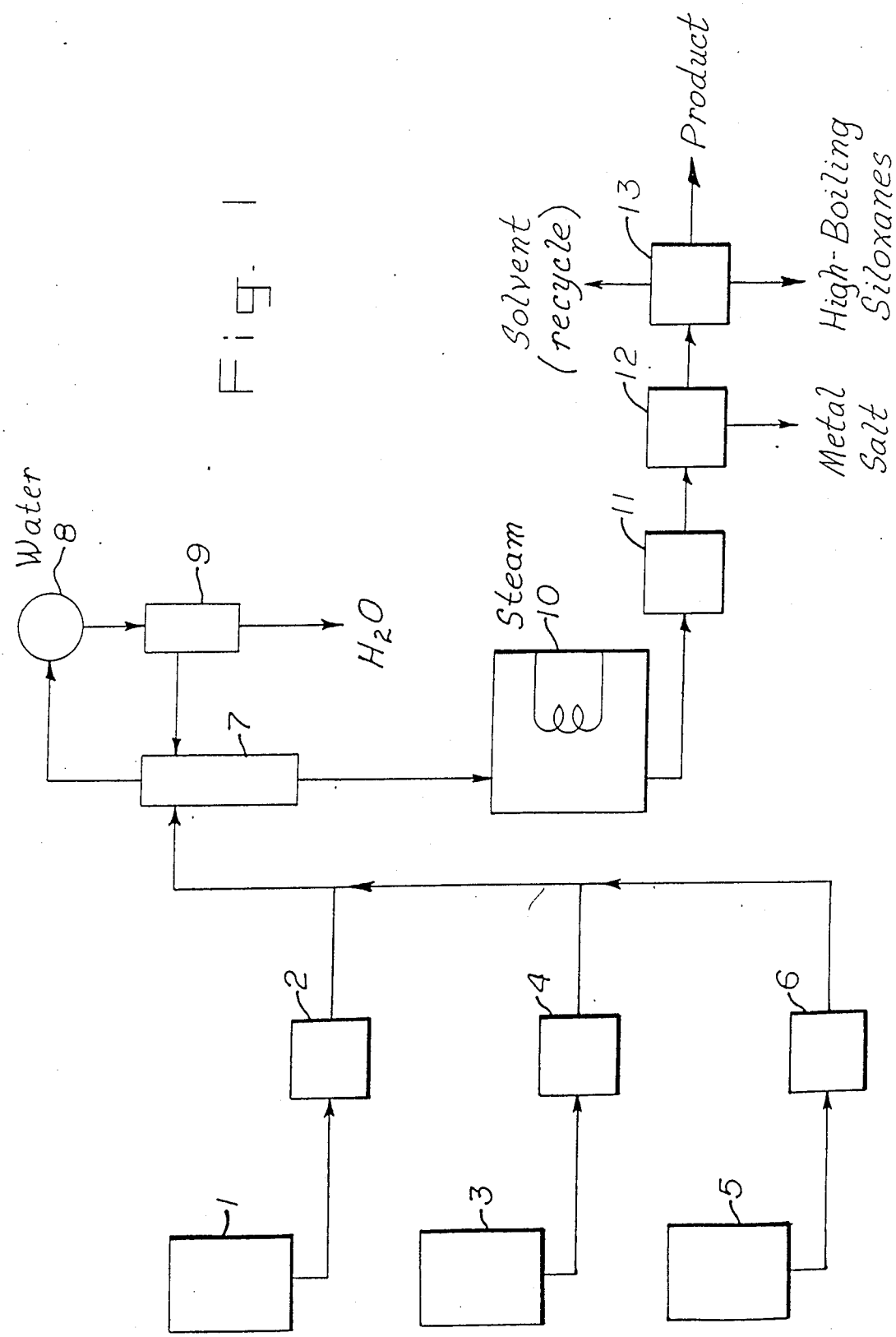

PROCESS FOR PREPARATION OF CYCLOPOLYDIORGANOSILOXANES

BACKGROUND OF THE INVENTION

This invention relates to a process for producing cyclopolydiorganosiloxanes. More specifically, this invention relates to a process which minimizes the cleavage of organic groups from silicon atoms while the cyclopolydiorganosiloxanes are being prepared and which improves the quality of the final product cyclopolydiorganosiloxanes.

To aid in the understanding of the instant invention, the following chemical definitions and notations are used herein:

"Polydiorganosiloxanes" means a. Cyclopolydiorganosiloxanes of the general formula,

$(R'R''SiO)_x$, wherein x has a value of at least 3;

b. Linear polydiorganosiloxanes of the general formula,

$HO(R'R''SiO)_vH$, wherein v has a value of at least 2; and c. A mixture of a. and b.; this mixture can include the product of hydrolysis of a diorganodihalosilane.

"Cyclopolydiorganosiloxanes" other than convertible cyclopolydiorganosiloxanes means the desired product which is a mixture that contains cyclopolydiorganosiloxanes having the general formulae,

$(R'R''SiO)_w$, $(R'R''SiO)_y$, and $(R'R''SiO)_z$, wherein w has a value of 3, y has a value of 4, and z has a value of 5.

"Branching", as used in the instant invention, means trifunctionality or tetrafunctionality caused by the cleavage of organic groups from the polydiorganosiloxane structure. This cleavage is represented by the following reaction scheme:

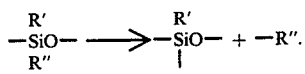

Branching is expressed as branched sites per million silicon atoms or parts per million branching.

Details on the chemical structure and notation will be set forth infra in this specification.

A significant quality issue with cyclopolydiorganosiloxanes is the branching content of the cyclopolydiorganosiloxanes which is caused by the cleavage of organic groups from the silicon atoms. Cleavage is particularly a problem with the vinyl and phenyl moieties on silicon. Siloxanes with a low level of branched sites are needed in the preparation of high-molecular weight diorganosiloxane polymers and their subsequent use in silicone elastomers.

The objectives of the instant invention are: (1) maximizing the yield of cyclopolydiorganosiloxanes; (2) minimizing the thermal or chemical cleavage of organic groups from silicon atoms; and (3) providing for a continuous reaction scheme for the preparation of cyclopolydiorganosiloxanes.

Most of the art that has been disclosed prior to the instant invention deals with the preparation of cyclopolydiorganosiloxanes by the thermal "cracking" or depolymerization of polydiorganosiloxanes in which the polydiorganosiloxanes are reacted with base catalysts to form the cyclopolydiorganosiloxanes, the cyclopolydiorganosiloxanes being continuously removed from the reaction zone by fractionation or other means of separation.

Hunter et al., J. Am. Chem. Soc., 68(1946), pp. 667-672, describe a method for preparing cyclic polydimethylsiloxanes of three to eight members from the product of the hydrolysis of dimethyldichlorosilane. A combination of distillation and depolymerization at temperatures up to 300°-400° C. using sodium hydroxide as a catalyst is disclosed. Individual cyclic polydimethylsiloxane species are isolated from the crude mixture of cyclic materials by fractional distillation.

Hyde in U.S. Pat. No. 2,438,478, issued March 23, 1948, and in U.S. Pat. No. 2,455,999, issued Dec. 14, 1948, discloses a process for recovering low-molecular weight cyclic polydimethylsiloxanes. The process is similar to that described by Hunter et al. above.

York in U.S. Pat. No. 2,816,124, issued Dec. 10, 1957, discloses a process for preparing hexaethylcyclotrisiloxane. This process utilizes limited amounts of alkaline-potassium catalyst such as hydroxide, carbonate, alcoholate, silanolate, and the like; heating high-molecular weight polydiorganosiloxanes under vacuum at 150°-250° C. with continuous removal of the cyclotrisiloxane.

Fletcher in U.S. Pat. No. 2,860,512, issued Nov. 11, 1958, discloses a method for preparing cyclic polydiorganosiloxanes by a "cracking" procedure in which polydiorganosiloxane materials are reacted with a hydroxide of Li, Na, K, or Cs in the presence of a high-boiling, inert solvent. The system is operated at high temperature and reduced pressure such as 225°-230° C. at atmospheric pressure and 130°-150° C. at 15-20 mm Hg. The solvent is used to overcome high viscosity or gellation in the reactor. This disclosure does not appear to deal with means to lessen the cleavage of organic groups.

Gordon in U.S. Pat. No. 2,884,432, issued April 28, 1959, discloses a process for preparing cyclic siloxanes in which triorganosiloxane materials are used to cause the contents of the cracker pot to remain fluid and to reduce the temperature of cracking for thermally less stable copolymers. Alkaline catalysts and temperatures of 150°-160° C. at 10-20 mm Hg are described. No mention is made of the impact of this invention on the quality of the final product.

Pierce and Holbrook in U.S. Pat. No. 2,979,519, issued April 11, 1961, disclose a process for the preparation of $[(F_3CCH_2CH_2)(CH_3)SiO]_3$ via "cracking" with fractionation. Catalysts utilized were KOH and LiOH. Temperatures of 200° to 400° C. were utilized. No mention is made of the problem of cleavage of organic groups.

Guinet and Puthet in U.S. Pat. No. 3,484,469, issued Dec. 19, 1969, disclose a process for preparing 1,3,5,7-tetramethyl-1,3,5,7-tetraphenylcyclosiloxane using an alkali metal carbonate as a catalyst in a "cracker" configuration. While improved yields are claimed, no mention is made of any improvement in final product quality by minimizing cleavage of the phenyl groups. Temperatures of 250°-290° C. were utilized.

Kuznetsova et al in U.S. Pat. No. 3,558,681, issued Jan. 26, 1971, disclose a process for the preparation of methylphenylcyclotri- and tetrasiloxanes by "cracking" using LiOH or lithium silanolate as the rearrangement catalyst. Temperatures of 250°–360° C. were used. Again, improved yields are claimed but no mention of any improvement in minimizing cleavage of phenyl groups, or any improvement in final product quality is made.

Macher in U.S. Pat. No. 3,607,898, issued Sept. 21, 1971, discloses a process for preparing cyclic symtetramethyltetravinyltetrasiloxane employing LiOH and a cocatalyst in a "cracking" configuration. Temperatures of 155°–160° C. at 20–30 mm Hg were utilized. While the problems of gellation in the reactor and low yields are lessened by this invention, there is no apparent reference to a measured improvement in lowering the tri- or tetrafunctionality of the final cyclopolyorganosiloxanes. A disadvantage of this disclosure compared to the instant invention is the need to use expensive cocatalysts such as alkylpolyethers and triphenylphosphine oxide.

Razzano in U.S. Pat. No. 3,846,464, issued Nov. 5, 1974, discloses a process for preparing symtetramethyltetravinyltetrasiloxane by cracking methylvinylpolysiloxanes with KOH and a high-boiling solvent. Temperatures in the cracking reactor were cited as 160°–165° C. at 20–30 mm Hg. As with the above cited patent by Fletcher, this disclosure deals with keeping the reaction mixture at a low viscosity and does not appear to address the problem of cleavage of organic groups.

Okamoto and Yanagisawa in U.S. Pat. No. 3,989,733, issued Nov. 2, 1976, disclose a combination "cracking" and rectification process in a column type reactor which uses as the column packing an alkaline catalyst in the form of pellets or an inert material upon which the alkaline catalyst is fused. Temperature and pressure conditions disclosed for the reaction zone were varied from 170°–270° C. and from 20 mm–760 mm Hg, respectively. While this disclosure improves on the semi-batch, semi-continuous schemes outlined above, the issue of improved quality due to reduced cleavage of organic groups does not appear to be addressed.

Finally, Bluestein in U.S. Pat. No. 4,111,973, issued Sept. 5, 1978, discloses a process for preparing a cyclotrisiloxane in a cracking reaction. This invention is only operable on fluoroalkyl siloxanes. Improved yields are claimed using higher aliphatic alcohols of 14 to 30 carbon atoms and temperatures above 150° C. No mention is made of the quality of the final product.

Two disadvantages appear inherent in these prior art approaches to preparing cyclopolydiorganosiloxanes. First, in most cracker configurations, even though the cyclopolydiorganosiloxanes are continuously removed from the reaction zone, a portion of siloxane materials is continuously in contact with the basic catalyst at elevated temperatures during the course of an extended run. It has been found, as illustrated in the examples infra, that prolonged contact of the polydiorganosiloxanes with a base catalyst at reaction temperature significantly increase the organic group cleavage. Concentration of the base catalyst relative to the polydiorganosiloxanes also significantly impacts upon organic group cleavage. The two-step reactor configuration of the instant invention would have a total residence time of approximately 1 hour. Secondly, the use of vacuum in an apparent attempt to lower the cracking temperature poses potential processing problems when using hydroxy-endblocked polydiorganosiloxanes as feed materials. The generation of water, particularly in a continuous reaction configuration, could result in foaming which significantly complicates reactor pressure control. Further, this foaming due to the liberation of water vapor under reduced pressure causes carry-over of the basic catalyst into a fractionation or stripping device and causes polymerization of the cyclosiloxane product and subsequent gellation.

Several unexpected findings were discovered during the development of the instant invention. It was found that the reaction of hydroxy-endblocked polydiorganosiloxanes proceeded in two distinct steps: (1) a reaction to form water; and (2) rearrangement of polydiorganosiloxanes to form cyclopolydiorganosiloxanes. It was found that the reaction to form water proceeded much more rapidly than the rearrangement reaction (approximately an order of magnitude faster). A continuous reactor scheme was developed which allowed these reactions to proceed essentially separately.

A low-boiling solvent is used in the process for two purposes: (1) to shift the chemical equilibrium to yield a maximum cyclopolydiorganosiloxane content in the reactor effluent, a phenomenon known in the art (Carmichael et al., J. Phys. Chem., 71:7 (1967), pp. 2011–2015, discuss the effect of solvent dilution upon the equilibrium between dimethylsiloxane cyclics and linears); and (2) to form a two-phase azeotrope to remove water from the reactor system. The latter point is important, since it was found unexpectedly that the presence of water during the rearrangement reaction shifted the chemical equilibrium away from the product cyclopolydiorganosiloxanes in favor of linear polydiorganosiloxanes. It was found that in using a reaction mixture that was at least 70 weight percent solvent, the siloxane fraction of the mixture was approximately 70 weight percent or more of the desired cyclopolydiorganosiloxane (cyclic trimer, -tetramer, and -pentamer), if the water of reaction was removed before the rearrangement reaction. If the water of reaction was not removed prior to the rearrangement reaction, the cyclopolydiorganosiloxane content was lowered to approximately 60 weight percent. The impact of water on the equilibration of polydiorganosiloxanes is outlined in the examples.

The desired cyclopolydiorganosiloxanes can be separated from the solvent and higher-boiling siloxane materials by conventional means such as distillation. An unexpected finding in the recovery of the cyclopolydiorganosiloxanes was the discovery that branched species were distributed throughout the siloxane fraction. For purposes of this invention and in order to follow the reaction, identification and measurement of branched species was facilitated by a special gas chromatographic analysis technique. The findings herein indicate that the minimizing of cleavage during the reaction to form the cyclopolydiorganosiloxanes is critical in controlling the branching content of the final product. The apparent shortcomings of the cracking technique in this regard have been described above.

DESCRIPTION OF THE DRAWING

The process of the instant invention will be described with reference to the accompanying drawing, FIG. 1. A schematic block flow diagram will be used to illustrate the apparatus that can be used.

In the drawing, FIG. 1, 1 is a feed tank for the polydiorganosiloxane feed; 2 is a means to feed the polydiorganosiloxane to the reactor system; 3 is a feed tank for the solvent used in the reaction; 4 is a means to feed the solvent to the reactor system; in actual practice, the polydiorganosiloxanes and the solvent can be combined into a single feed tank and a single feed means; 5 is a feed tank for the catalyst; 6 is a means to feed the catalyst to the reactor system; 7 is a column-type device in which the polydiorganosiloxanes are reacted with the catalyst to generate water; the column-type device can be of such a configuration as a bubble-cap tray column or can be a packed column or the like; 8 is a condenser in which solvent and water vapors which pass up through the column-type device are condensed; 9 is a trap in which the water generated is collected and removed and from which condensed solvent vapors are returned to the column-type device as liquid reflux; 10 is the reactor in which the polydiorganosiloxanes, essentially freed of water, are rearranged to produce the desired cyclopolydiorganosiloxanes; 11 is a vessel, such as a continuous stirred tank reactor in which the catalyst can be neutralized with a diorganodichlorosilane; carbon dioxide, a carboxylic acid, or the like, if desired; 12 is a filter or like device to remove the salts from catalyst neutralization from the reactor effluent, if desired; 13 is the final product recovery system in which the solvent can be recovered and recycled to the reactor system and in which the final cyclopolydiorganosiloxanes are recovered from higher-boiling polydiorganosiloxanes, the higher-boilers potentially being recycled to the reactor system.

DESCRIPTION OF THE INVENTION

In accordance with the instant invention there is provided a process to produce and recover cyclopolydiorganosiloxanes of improved quality, the process comprising the reaction of polydiorganosiloxanes under conditions as will be delineated herein. What is described, therefore, is a process for converting polydiorganosiloxanes to cyclopolydiorganosiloxanes with reduced cleavage of organic groups from silicon atoms, said process comprising (I) mixing and contacting the polydiorganosiloxanes with a catalyst and with an organic solvent which is capable of forming a two-phase azeotrope with water; (II) feeding the mixture of (I) to a device in which water is formed as the polydiorganosiloxanes react in the presence of the catalyst and the organic solvent, the water formed being driven out of said device as a two-phase organic solvent, water azeotrope, the reaction being facilitated by heat furnished by refluxing of the organic solvent; (III) reacting the polydiorganosiloxane, catalyst, organic solvent mixture from (II), which is essentially free of water, to convert said polydiorganosiloxanes to said cyclopolydiorganosiloxanes.

"Reduced cleavage of organic groups from silicon atoms", as used in the instant invention, means minimizing the following reaction during preparation of the desired product cyclodiorganosiloxanes:

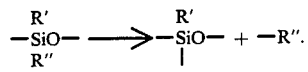

Cleavage of organic groups from silicon atoms is minimized by use of a minimum level of catalyst at as low a reaction time and temperature as is practical. The examples, infra, demonstrate that the level of cleavage or branching can be varied as much as fivefold or more.

The polydiorganosiloxanes, as described above, can be the product of hydrolysis of a diorganodihalosilane of the formula, $$R'R''SiX_2,$$

wherein R' and R'' are independently selected from a group which consists essentially of methyl, ethyl, phenyl, trifluoropropyl, and vinyl groups, and X is chlorine or bromine. The product of the above hydrolysis reaction is a mixture of linear and cyclic polydiorganosiloxane materials. The general formulae for these two convertible polydiorganosiloxane species are:

$$\text{Linears} = HO(R'R''SiO)_v H$$

$$\text{Cyclics} = (R'R''SiO)_x,$$

wherein x has a value of at least 3, and v has a value of at least 2. Some examples of the polydiorganosiloxanes species are:

$$HO[(CH_3)_2 SiO]_v H,$$

$$[(CH_3)(C_2H_5)SiO]_x,$$

$$HO[(C_6H_5)(CH_3)SiO]_v H,$$

$$[(F_3CCH_2CH_2)(CH_3)SiO]_x, \text{ and}$$

$$HO[(CH_3)(CH_2=CH)SiO]_v H.$$

The polydiorganosiloxanes may be a linear material as has just been described above. The polydiorganosiloxanes may also be cyclic material, as described above, or any mixture of linear and cyclic siloxane materials.

The catalyst for the process can be an alkali metal hydroxide which is selected from a group which consists essentially of lithium, sodium, potassium, and cesium hydroxides. The catalyst may also be an alkali metal silanolate which is selected from a group which consists essentially of lithium, sodium, potassium, and cesium silanolates.

The alkali metal hydroxide or silanolate is present in the reaction mixture at a molar proportion relative to the polydiorganosiloxanes of at least 200 parts per million. An upper limit of 5000 parts per million alkali metal hydroxide or silanolate relative to the polydiorganosiloxanes is established as a practical limit at which the process operating conditions can be optimized and yet reduce cleavage of organic groups from silicon atoms.

The solvent in the process serves a two-fold purpose: (1) formation of a two-phase azeotrope with water, which is formed by the reaction of the hydroxy-endblocked linear polydiorganosiloxanes with an alkali metal hydroxide or silanolate in the presence of the solvent, to facilitate separation of the water; and (2) shifting the chemical equilibrium during the rearrangement reaction to maximize the yield of the desired product cyclopolydiorganosiloxane materials. The solvent can be selected from a group which consists essentially of hexane, heptane, toluene, and xylene. The organic solvent is present in the reaction mixture at a weight proportion relative to the polydiorganosiloxanes of at least 70%. From the known art, a solvent content of at least 70% is needed to maximize the equilibrium content of the desired product cyclopolydiorganosiloxanes in the solvent, polydiorganosiloxane mixture.

"Contacting" and "mixing" of the polydiorganosiloxanes, the organic solvent, and the catalyst, means the introduction of these materials to the device in which water is formed. These three materials may be fed to the system separately by conventional means such as a pump. These materials may be combined, one with another or all three together, in a conventional means such as a mixing tank and fed by conventional means. The materials, if fed separately, may be contacted and mixed prior to the device in which water is formed by conventional means such as an in-line mixer. The materials may also be fed to the device in which water is formed at which point the materials will be intimately contacted and mixed by the refluxing system that will be discussed in the following paragraph.

Any device in which water can be formed by the reaction of the polydiorganosiloxanes in the presence of an alkali metal hydroxide or silanolate and an organic solvent is useful herein. Conventional devices, such as a packed column or a tray column such as a bubble-cap column or a sieve-tray column, with a relatively short contact or residence time are especially useful herein. "Short contact time" for purposes of this invention range from about 1 minute to about 5 minutes. The residence time should be at least 1 minute. As shown in the drawing, FIG. 1, the polydiorganosiloxanes, the solvent, and the catalyst are fed to the upper portion of the column. Heat input to the column is supplied by the reactor, as will be described in the following paragraph. Solvent vapors and refluxing liquid are in intimate contact with the polydiorganosiloxanes which are flowing down the column. Water which is formed by the reaction is driven up the column with solvent vapor. Solvent and water vapors are condensed, the water is trapped and drawn off, and the solvent is returned to the column as reflux. The volumetric flow rate of solvent reflux to the column is maintained at a volumetric flow rate of at least 25% of the flow rate of the reaction mixture. This minimum reflux of solvent is specified to assure that there is proper contact between the liquids and vapors in the column, consistent with known art in the design of such devices. The reflux flow rate is controlled by the heat input to the reactor.

Solvent, polydiorganosiloxanes, and the catalyst are then fed to the reactor in which the rearrangement reaction to form the final product cyclopolydiorganosiloxanes is effected. Residence time of the reaction mixture in the reactor is at least 15 minutes. A residence time of 15 minutes is essentially the minimum reaction time needed to rearrange the polydiorganosiloxanes in the reaction mixture to the desired product cyclopolydiorganosiloxane. The system is run at atmospheric pressure, and as a result, the temperature of the system is the boiling point of the polydiorganosiloxane, solvent mixture. Heat to the reactor and said device, is supplied by external means such as a heated coil within the reactor, or an external jacket on the reactor, or other means of external heating known in the art of such reactor design.

The polydiorganosiloxane, solvent, catalyst mixture then passes to a vessel, such as a continuous stirred tank reactor, in which the catalyst can be neutralized with an acidic material. The acidic material which can be used to neutralize the catalyst are such materials as the corresponding diorganodihalosilane (i.e., $(CH_3)_2SiCl_2$ in the case of $[(CH_3)_2SiO]_x$, $(CH_3)(CH_2\!=\!CH)SiCl_2$ in the case of $[(CH_3)(Ch_2\!=\!CH)SiO]_x$, and the like), carbon dioxide, carboxylic acids, or the like. The salts formed during neutralization can be removed by conventional means such as a filter or the like.

The neutralized, salt-free polydiorganosiloxane, solvent solution can then be passed to a conventional fractional distillation system in which the desired cyclopolydiorganosiloxanes are recovered. The solvent can be removed from the feed solution by conventional distillation. The solvent can be recycled to the reactor system. The desired product cyclopolydiorganosiloxanes are then distilled from higher-boiling polydiorganosiloxanes. The desired product cyclopolydiorganosiloxanes are a mixture which has the formulae,

$(R'R''SiO)_w$, $(R'R''SiO)_y$ and $(R'R''SiO)_z$, wherein, w has a value of 3, y has a value of 4, and z has a value of 5. The higher-boiling polydiorganosiloxanes, mainly higher molecular weight cyclopolydiorganosiloxanes may be recycled as feed to the reactor.

PREFERRED EMBODIMENT OF THE INVENTION

The preferred mode of carrying out the instant invention is to feed polydiorganosiloxanes, an aqueous potassium hydroxide solution, and toluene to the top of a bubble-cap column in which toluene is refluxing, the heat being inputted in the lower reactor. The feed ratio of potassium hydroxide to polydiorganosiloxane is 400 to 2500 parts per million potassium on a molar basis relative to the polydiorganosiloxane. The heat input should be controlled so that the reflux of solvent back to the column is 25 to 250% of the combined feed rates of the reaction mixture. Feed rates are maintained so that the residence time of the polydiorganosiloxanes in the column is about 1 to 5 minutes. Correspondingly, feeds are regulated or the reactor is sized so that the residence time of the reaction mixture in the reactor is about 15 to 120 minutes.

The system is preferably operated at atmospheric pressure and the system temperature is the boiling point of the toluene, polydiorganosiloxane mixture. Solvent and polydiorganosiloxane feeds should be controlled so that the reaction mixture in the reactor is 70 to 80 weight percent toluene.

The toluene, polydiorganosiloxane, potassium hydroxide mixture leaving the reactor can be treated with the corresponding diorganodichlorosilane, as described supra, to neutralize the potassium hydroxide. The solvent, polydiorganosiloxane mixture can then be passed through a filter to remove the resultant potassium chloride salts. The neutralized solvent solution can then be stripped of toluene by conventional distillation, and the toluene can be recycled to the reaction. The solvent-free polydiorganosiloxane mixture is distilled by conventional means to recover the desired $(R'R''SiO)_w$, $(R'R''SiO)_y$, $(R'R''SiO)_z$ mixture. The residual higher-boiling polydiorganosiloxanes are potentially recycleable as a feed material for the instant process.

The following examples are presented to be illustrative of the instant invention and are not to be construed as limiting the instant invention delineated in the claims.

EXAMPLE 1

A run was made to demonstrate the instant invention.

The reactor system consisted of a bubble-cap column above a pot-type reactor. The bubble-cap column was 1 inch in diameter and 6 inches tall. The column had six bubble-cap trays. The bubble-cap column was fitted with a water-cooled condenser and a Dean-Stark trap to allow water to be trapped from the condensed vapors from the column and with provisions to allow the condensed volatile organic solvent to return to the column as reflux. The reactor had a volume of 300 ml. and was fitted to provide the heat input to the system.

A product of hydrolysis of methylvinyldichlorosilane was the source of polydiorganosiloxanes. The product of hydrolysis was analyzed by gas chromatography and the analysis of the hydrolyzate was as follows:

$[(CH_3)(CH_2=CH)SiO]_x = 59$ weight percent $HO[(CH_3)(CH_2=CH)SiO]_yH = 41$ weight percent The polymethylvinylsiloxane material was diluted with toluene to yield a feed solution of 29 weight percent polymethylvinylsiloxane in toluene.

The system was started up by charging toluene to the reactor. The reactor was heated so that the toluene was boiling and was refluxing in the bubble-cap column. The heat input to the reactor was controlled so that the reflux to the column was approximately 25% of the flow rate of the incoming toluene, siloxane feed solution.

The toluene, siloxane feed solution was fed to the top of the bubble-cap column at a flow rate of 4.5 ml/min. An aqueous potassium hydroxide solution, 38 weight percent KOH in water, was fed at a flow rate of 0.0012 ml/min to the top of the column. These feed rates gave a catalyst concentration of 880 parts per million K in siloxane on a mole basis.

The feed rates and the volumes of the bubble-cap column and the reactor resulted in residence times of 2 minutes and 40 minutes in the bubble-cap column and the reactor, respectively. The equilibrated polymethylvinylsiloxane solution was collected continuously from an overflow from the reactor, neutralized with methylvinyldichlorosilane, and was analyzed by gas chromatography. The siloxane portion of the solution had the following composition, expressed in weight percent:

Cyclic trimer thru pentamer—73.9%

The siloxane portion of the above solution was further analyzed by gas chromatography to measure the branching or degree of vinyl group cleavage. The sample was analyzed to have a branching content of approximately 142 parts per million, based upon the molar ratio of branched to difunctional siloxane species.

This example demonstrates the instant invention. Further, this example demonstrates the high conversion of siloxanes to the desired cyclic material. Additionally, this example details a measure of the degree of vinyl cleavage.

EXAMPLE 2

85 grams of the product of hydrolysis of methylvinyldichlorosilane was charged to an agitated batch reactor along with 210 grams toluene and 0.073 ml of 45 weight percent potassium hydroxide in water. This charge of potassium hydroxide resulted in a catalyst concentration of 860 parts per million in siloxane on a mole basis. The batch reactor was heated and fitted with a water-cooled condenser to condense volatiles boiling from the reactor. A Dean-Stark trap was installed after the condenser to trap out any water before the toluene was returned to the reactor.

The reactor and its contents were heated, toluene was allowed to boil up and reflux back to the column, and water was collected in the Dean-Stark trap. The above conditions resulted in a reactor temperature of 109° C.

Samples were taken over a period of 2 hours. The samples were analyzed by gas chromtography for weight percent total cyclics in the siloxane portion of the reaction mixture, weight percent of desired cyclics (denoted below as % $C_3$-$C_5$), and weight percent of total polydiorganosiloxanes that $C_3$-$C_5$ represent (denoted by % Siloxane). These samples are designated as Samples A, B, and C, respectively. The results of these analyses are listed below in Table 1 as a function of reaction time.

TABLE 1

| Sample | Time, min | % Total Cyclics | % $C_3$-$C_5$ | % Siloxane |
|---|---|---|---|---|
| A | 1 | 52 | 92.6 | 48.1 |
| B | 22 | 83 | 84.5 | 70.1 |
| C | 113 | 87 | 84.9 | 73.8 |

A second run was made using the above procedures, with the exception that the water formed during the reaction was not trapped and removed but was returned to the reaction vessel as reflux with the condensed toluene. Samples were again taken over a period of approximately 2 hours. The samples were analyzed as above by gas chromatography, and the results are summarized in Table 2. These samples are designated Samples D, E, and F, respectively.

TABLE 2

| Sample | Time, min | % Total Cyclics | % $C_3$-$C_5$ | % Siloxane |
|---|---|---|---|---|
| D | 3 | 56 | 84.6 | 47.3 |
| E | 18 | 72 | 85.5 | 61.5 |
| F | 108 | 73 | 84.4 | 61.6 |

This example demonstrates the impact of time at temperature on the conversion of siloxane materials to the desired cyclosiloxanes. More significantly, the above results demonstrate that conversion of the polydiorganosiloxanes to the desired cyclopolydiorganosiloxanes is inhibited when water is not removed from the reaction zone as it is formed.

EXAMPLE 3

(Not Within the Scope of the Instant Invention)

Using the same general procedures as outlined in Example 2 with a 750-gal. batch reactor (loaded with 1600 lbs. of polymethylvinylsiloxanes and 4000 lbs. of toluene), three runs were made at varying levels of potassium hydroxide. Reactor contents were sampled as the runs progressed, and samples were analyzed by gas chromatography for parts per million branching. These samples were designated as Samples A, B, C, D, E, F, G, H, I, J, K, and L, respectively. Table 3 is a summary of these analyses. Reaction time is denoted as Time, hr; catalyst concentration (parts per million K relative to siloxane on a molar basis) is denoted as ppm K; branching sites per million moles of silicon are denoted as ppm branching.

TABLE 3

| Sample | Time, hr | ppm K | ppm Branching |
|---|---|---|---|
| A | 5 | 1720 | 5,458 |
| B | 8 | ′ | 5,718 |
| C | 12 | ′ | 8,517 |
| D | 16 | ↓ | 11,236 |
| E | 5 | 1290 | 2,691 |
| F | 8 | ′ | 2,857 |
| G | 12 | ′ | 5,826 |
| H | 16 | ↓ | 7,594 |
| I | 5 | 860 | 2,163 |
| J | 8 | ′ | 2,243 |
| K | 12 | ′ | 2,794 |
| L | 16 | ↓ | 3,406 |

These above results demonstrate the impact of residence time and alkali metal hydroxide concentration on the branching or vinyl cleavage of the final cyclopolydiorganosiloxane crude.

EXAMPLE 4

A series of runs was made with the reactor system of the instant invention to determine the effect of several of the reaction variables upon the cleavage of the product of reaction.

The reactor system is the same as that described in Example 1.

The polydiorganosiloxane feed used during this study was a mixture of (1) the hydrolysis product of methylvinyldichlorosilane; and (2) a hydroxy-endblocked linear polymethylvinylsiloxane. The siloxane mixture was approximately 50 weight percent each of the hydrolysis product and the linear siloxanes. The combined siloxane mixture had been analyzed by gas chromatography and found to have 1514 parts per million (ppm) branching.

As in Example 1, the system was started up with toluene. The reactor was heated so that the reflux to the column would be approximately 40% of the flow of the combined toluene, polymethylvinylsiloxane feed.

The toluene and siloxanes were combined as a common feed. The mixture was adjusted so that the siloxane content was 29 weight percent siloxane.

The toluene, siloxane mixture and a 38 weight percent aqueous potassium hydroxide solution were fed to the top of the column. Flow rates of these two feeds were varied to alter residence times in both the column and the reactor and the potassium concentration in the reaction system. The product from the reactor overflowed into a stirred vessel into which sufficient methylvinyldichlorosilane was added to neutralize the potassium hydroxide. Samples of the toluene, siloxane reaction solution were analyzed by gas chromatography for branching.

Residence time in the bubble-cap column was varied from 1 to 3 minutes. Residence time in the reactor was varied from 15 to 105 minutes. Potassium concentration in the reactor system was varied from 400 to 2200 parts per million relative to polydiorganosiloxanes on a molar basis.

The absolute branching levels of the polydiorganosiloxane portion of the reaction solution ranged from 1729 to 3441 ppm. Assuming that the feed contributed 1514 ppm branching, the net branching formation ranged from 215 to 1927 ppm.

The above results demonstrate that reaction conditions can be varied to control the level of branching in the final cyclosiloxanes. The level of branching attained can be significantly lower than that achieved with a conventional batch equilibration process in which longer reaction times are utilized.

What we claim is:

1. A process for converting polydiorganosiloxanes to cyclopolydiorganosiloxanes with reduced cleavage of organic groups from silicon atoms, said process comprising (I) mixing and contacting the polydiorganosiloxanes with a catalyst and with an organic solvent which is capable of forming a two-phase azeotrope with water; (II) feeding the mixture of (I) to a device in which water is formed as the polydiorganosiloxanes react in the presence of the catalyst and the organic solvent, the water formed being driven out of said device as a two-phase organic solvent, water azeotrope, the reaction being facilitated by heat furnished by refluxing of the organic solvent; (III) reacting the polydiorganosiloxane, catalyst, and organic solvent mixture from (II), which is essentially free of water, to convert said polydiorganosiloxanes to said cyclopolydiorganosiloxanes.

2. The process according to claim 1, wherein the polydiorganosiloxanes are the product of hydrolysis of a diorganodihalosilane, said diorganodihalosilane having the formula, R'R"SiX$_2$, wherein, R' and R" are independently selected from a group which consists essentially of methyl, ethyl, phenyl, trifluoropropyl, and vinyl group, and X is chlorine or bromine.

3. The process according to claim 1, wherein the polydiorganosiloxanes are a hydroxyl-endblocked linear polydiorganosiloxane of the formula, HO(R'R"SiO)$_v$H, wherein R' and R" are independently selected from a group which consists essentially of methyl, ethyl, phenyl, trifluoropropyl, and vinyl groups, and v has a value of at least 2.

4. The process according to claim 1, wherein the convertible polydiorganosiloxanes are cyclopolydiorganosiloxane of the formula, (R'R"SiO)$_x$, wherein R' and R" are independently selected from a group which consists essentially of methyl, ethyl, phenyl, trifluoropropyl, and vinyl groups, and x has a value of at least 3.

5. The process according to claim 1, wherein the polydiorganosiloxanes are a mixture of HO(R'R"SiO)$_v$H and (R'R"SiO)$_x$.

6. The process according to claim 1, wherein the catalyst is an alkali metal hydroxide selected from the group which consists essentially of lithium, sodium, potassium, and cesium hydroxides.

7. The process according to claim 1, wherein the catalyst is an alkali metal silanolate selected from the group which consists essentially of lithium, sodium, potassium, and cesium silanolates.

8. The process according to claim 6, wherein the alkali metal hydroxide is present in the reaction mixture at a molar proportion relative to the polydiorganosiloxanes of at least 200 parts per million.

9. The process according to claim 7, wherein the alkali metal silanolate is present in the reaction mixture at a molar proportion relative to the polydiorganosiloxane of at least 200 parts per million.

10. The process according to claim 1, wherein the organic solvent which forms a two-phase azeotrope with water is selected from a group which consists essentially of hexane, heptane, toluene, and xylene.

11. The process according to claim 10, wherein the solvent is present in the reaction mixture at a weight proportion of at least 70%.

12. The process according to claim 1, wherein the residence time of the reaction mixture in the device in which water is formed is at least 1 minute.

13. The process according to claim 1, wherein the residence time for the reaction mixture in the reactor is at least 15 minutes.

14. The process according to claim 1, wherein the process is carried out at atmospheric pressure.

15. The process according to claim 1, wherein the system temperature is the boiling-point of the polydiorganosiloxane and organic solvent mixture.

16. The process according to claim 1, wherein the product cyclopolydiorganosiloxanes are a mixture containing cyclopolydiorganosiloxanes of the formulae, $(R'R''SiO)_w$, $(R'R''SiO)_y$ and $(R'R''SiO)_z$, wherein, w has a value of 3, y has a value of 4, and z has a value of 5; and wherein R' and R'' are independently selected from a group which consists essentially of methyl, ethyl, phenyl, trifluoropropyl, and vinyl groups.

17. The process according to claim 1, wherein the polydiorganosiloxanes are the product of the hydrolysis of methylvinyldichlorosilane; the catalyst is potassium hydroxide; the organic solvent is toluene; and the product cyclopolydiorganosiloxanes are a mixture of $[(CH_3)(CH_2=CH)SiO]_w$, $[(CH_3)(CH_2=CH)SiO]_y$, and $[(CH_3)(CH_2=CH)SiO]_z$, wherein w has a value of 3, y has a value of 4, and z has a value of 5.

18. The process according to claim 1, wherein the polydiorganosiloxanes are a hydroxyl-endblocked linear polymethylvinylsiloxane of the formula, $HO[(CH_3)(CH_2=CH)SiO]_vH$, wherein, v has a value of at least 2; the catalyst is potassium hydroxide; the organic solvent is toluene; and the product cyclopolydiorganosiloxanes are a mixture of $[(CH_3)(CH_2=CH)SiO]_w$, $[(CH_3)(CH_2=CH)SiO]_y$, and $[(CH_3)(CH_2=CH)SiO]_z$.

19. The process according to claim 1, wherein the convertible polydiorganosiloxanes are cyclopolymethylvinylsiloxanes of the formula, $[(CH_3)(CH_2=CH)SiO]_x$, wherein, x has a value of at least 3; the catalyst is potassium hydroxide, the organic solvent is toluene; and the product cyclopolydiorganosiloxanes are a mixture of $[(CH_3)(CH_2=CH)SiO]_w$, $[(CH_3)(CH_2=CH)SiO]_y$, and $[(CH_3)(CH_2=CH)SiO]_z$.

20. The process according to claim 1, wherein the polydiorganosiloxanes are a mixture of $[(CH_3)(CH_2=CH)SiO]_x$ and $HO[(CH_3)(CH_2=CH)SiO]_vH$; the catalyst is potassium hydroxide; the organic solvent is toluene; and the product cyclopolydiorganosiloxanes are a mixture of $[(CH_3)(CH_2=CH)SiO]_w$, $[(CH_3)(CH_2=CH)SiO]_y$, and $[(CH_3)(CH_2=CH)SiO]_z$.

21. The process according to claim 17, wherein the toluene is present at a concentration of at least 70 percent by weight; the potassium hydroxide content is present in the reaction mixture at a molar proportion relative to the polydiorganosiloxanes of 400 to 2500 ppm; and the system is at atmospheric pressure.

22. The process according to claim 18, wherein the toluene is present at a concentration at least 70 percent by weight; the potassium hydroxide content is present in the reaction mixture at a molar proportion relative to the polydiorganosiloxanes of 400 to 2500 ppm; and the system is at atmospheric pressure.

23. The process according to claim 19, wherein the toluene is present at a concentration of at least 70 percent by weight; the potassium hydroxide content is present in the reaction mixture at a molar proportion relative to the polydiorganosiloxanes of 400 to 2500 ppm; and the system is at atmospheric pressure.

24. The process according to claim 20, wherein the toluene is present at a concentration of at least 70 percent by weight; the potassium hydroxide content is present in the reaction mixture at a molar proportion relative to the polydiorganosiloxanes of 400 to 2500 ppm; and the system is at atmospheric pressure.

* * * * *